United States Patent
Layton, Jr. et al.

(10) Patent No.: US 8,597,289 B2
(45) Date of Patent: Dec. 3, 2013

(54) CERVICAL OPENING SEALING DEVICES

(75) Inventors: Russell K. Layton, Jr., Acton, MA (US); Lionel Stewart MacLean, Allston, MA (US); David Freed, Westborough, MA (US); Brian Hanley, Framingham, MA (US)

(73) Assignee: Cytyc Corporation, Malborough, MA (US)

( * ) Notice: Subject to any disclaimer, the term of this patent is extended or adjusted under 35 U.S.C. 154(b) by 844 days.

(21) Appl. No.: 12/696,930

(22) Filed: Jan. 29, 2010

(65) Prior Publication Data

US 2010/0198214 A1    Aug. 5, 2010

Related U.S. Application Data

(60) Provisional application No. 61/148,725, filed on Jan. 30, 2009.

(51) Int. Cl.
*A61B 18/18* (2006.01)
*A61N 1/00* (2006.01)

(52) U.S. Cl.
USPC ............. 606/41; 604/515; 606/119; 607/138

(58) Field of Classification Search
USPC ......... 606/33, 41, 50, 119, 42, 45, 46, 48, 49; 604/515; 607/101–102, 113, 138; 128/838
See application file for complete search history.

(56) References Cited

U.S. PATENT DOCUMENTS

| | | | |
|---|---|---|---|
| 2,818,856 A * | 1/1958 | Kohl ............................. | 128/838 |
| 5,125,916 A * | 6/1992 | Panebianco et al. .......... | 604/332 |
| 5,542,928 A * | 8/1996 | Evans et al. ................... | 604/113 |
| 5,653,692 A * | 8/1997 | Masterson et al. ............ | 604/113 |
| 5,741,248 A * | 4/1998 | Stern et al. ...................... | 606/21 |
| 5,769,880 A | 6/1998 | Truckai et al. | |
| 6,547,784 B1 * | 4/2003 | Thompson et al. ............. | 606/21 |
| 6,813,520 B2 | 11/2004 | Truckai et al. | |

(Continued)

FOREIGN PATENT DOCUMENTS

| WO | 2004/035110 | 4/2004 |
|---|---|---|
| WO | 2007/126809 | 11/2007 |

OTHER PUBLICATIONS

PCT International Search Report and Written Opinion for PCT/US2010/022601, Applicant CYTYC Corp., Forms PCT/ISA/210, 220, and 237 dated Aug. 26, 2010 (16 pages).

(Continued)

*Primary Examiner* — Michael Peffley
*Assistant Examiner* — Khadijeh Vahdat
(74) *Attorney, Agent, or Firm* — Vista IP Law Group LLP

(57) ABSTRACT

A device for sealing a cervical opening includes a support structure, and a seal coupled to the support structure, the seal having a surface for abutting against tissue next to the cervical opening, wherein the seal is tiltable relative to the support structure. A device for sealing a cervical opening includes a support structure, and a member coupled to the support structure, wherein the member is inflatable to create a seal for abutting against cervical tissue. A device for sealing a cervical opening includes a seal having a surface for contacting tissue next to the cervical opening, an opening formed on the surface of the seal, and a vacuum port, wherein the opening is in fluid communication with the vacuum port.

11 Claims, 11 Drawing Sheets

(56) References Cited

U.S. PATENT DOCUMENTS

| | | | |
|---|---|---|---|
| 2003/0130575 A1* | 7/2003 | Desai | 600/417 |
| 2004/0215099 A1* | 10/2004 | Sampson et al. | 600/560 |
| 2005/0107818 A1* | 5/2005 | Valtchev | 606/193 |
| 2005/0267468 A1* | 12/2005 | Truckai et al. | 606/41 |
| 2006/0212043 A1* | 9/2006 | Grillo | 606/119 |

OTHER PUBLICATIONS

PCT Partial International Search Report PCT/US2010/022601, Applicant CYTYC Corp., Annex to Form PCT/USA/206, dated Jun. 23, 2010 (2 pages).

* cited by examiner

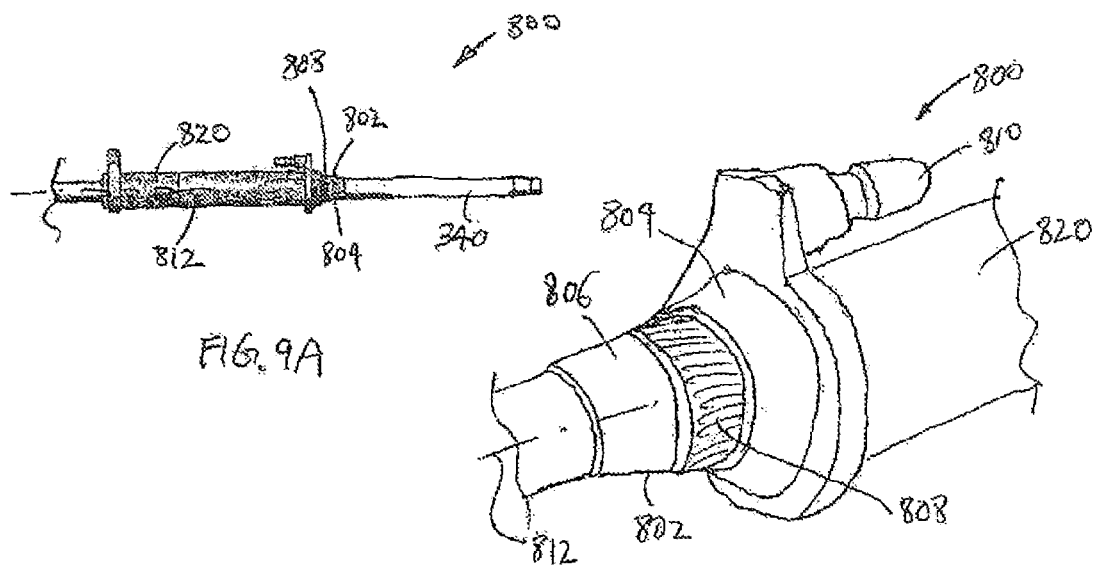
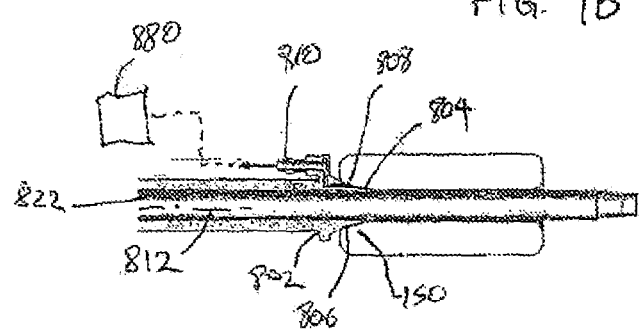
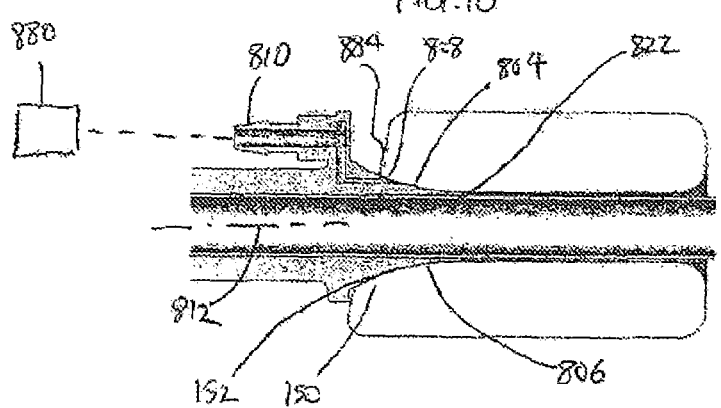

CERVICAL OPENING SEALING DEVICES

RELATED APPLICATION DATA

This application claims priority to and the benefit of U.S. Provisional Patent Application No. 61/148,725, filed on Jan. 30, 2009, the entire disclosure of which is expressly incorporated by reference herein.

FIELD

This application relates to systems and methods for sealing a cervical os.

BACKGROUND

There are certain medical procedures that are carried out within a body cavity. One example of such a procedure is tissue ablation. Ablation of the interior lining of a body organ is a procedure which involves heating the organ lining to temperatures which destroy the cells of the lining or coagulate tissue proteins. Such a procedure may be performed as a treatment to one of many conditions, such as chronic bleeding of the endometrial layer of the uterus or abnormalities of the mucosal layer of the gallbladder. Existing methods for effecting ablation include circulation of heated fluid inside the organ (either directly or inside a balloon), laser treatment of the organ lining, and resistive heating using application of RF energy to the tissue to be ablated.

Ablation procedures are often carried out without direct endoscopic visualization. For example, ablation of the endometrial layer typically involves insertion of an elongate ablation device into the patient's uterus, without the use of a hysteroscope. As can be appreciated, the presence of a perforation in the uterus could result in inadvertent passage of the ablation device through the perforation and out of the uterus into the region adjacent the bowel. Although events of this nature are rare, the injury that could result from such occurrences make it highly desirable to provide a mechanism by which a physician can evaluate whether perforations are present in a body cavity before a treatment device such as an ablation device is used to deliver power.

In one approach for detecting perforation in a body cavity, a fluid (either liquid or gas) is delivered into the body cavity to slightly pressurize the cavity. A pressure sensing system monitors the pressure within the cavity for a predetermined test period. If cavity pressure is not substantially sustained during the test period, the physician is alerted to further assess the cavity for perforations before initiating treatment within the cavity. As can be appreciated, in order for such technique to work, the cervical os must be sealed during the operation period of the pressure sensing system. Otherwise, fluid may leak out from the cervical os, resulting in a pressure reading that is inaccurate.

Existing devices for sealing cervical os may not provide a hermetic seal at the external cervical os. This is particularly the case when the external os is angled such that it is not perpendicular or normal to the axis of the sealing device. Also, in some cases, the cervix may lack the firmness (patulous cervix) required for a good seal. To address such problems, doctors have sutured the os (opening) tissue to form a purse string seal (called a circlage), and have used a tenaculum to pinch the seal-os interface. However, such fixes may complicate the procedure and may not provide a desirable result.

SUMMARY

In accordance with some embodiments, a device for sealing a cervical opening includes a support structure, and a seal coupled to the support structure, the seal having a surface for abutting against tissue next to the cervical opening, wherein the seal is tiltable relative to the support structure.

In accordance with other embodiments, a device for sealing a cervical opening includes a support structure, and a bellow coupled to the support structure, wherein the bellow has a first end for abutting against tissue next to the cervical opening.

In accordance with other embodiments, a device for sealing a cervical opening includes a support structure, and a member coupled to the support structure, wherein the member is inflatable to create a seal for abutting against cervical tissue.

In accordance with other embodiments, a device for sealing a cervical opening includes a seal having a tapered portion for inserting into the cervical opening, and a cover portion for abutting against external tissue of the cervical opening, the cover portion having a cross sectional dimension that is at least 1.5 inches.

In accordance with other embodiments, a device for sealing a cervical opening includes a support structure, and a seal coupled to the support structure, wherein the seal is sized for insertion at least partially into the cervical opening, and the seal is deformable to conform to a shape of the cervical opening.

In accordance with other embodiments, a device for sealing a cervical opening includes a seal having a surface for contacting tissue next to the cervical opening, an opening formed on the surface of the seal, and a vacuum port, wherein the opening is in fluid communication with the vacuum port.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIGS. 9A-B illustrate another device for sealing a cervical opening in accordance with other embodiments.

FIG. 10 illustrates the device of FIGS. 9A-B being used to seal a cervical opening that has a normal configuration.

FIG. 11 illustrates the device of FIGS. 9A-B being used to seal a cervical opening that has an angled configuration.

DESCRIPTION OF THE EMBODIMENTS

Figure 1:
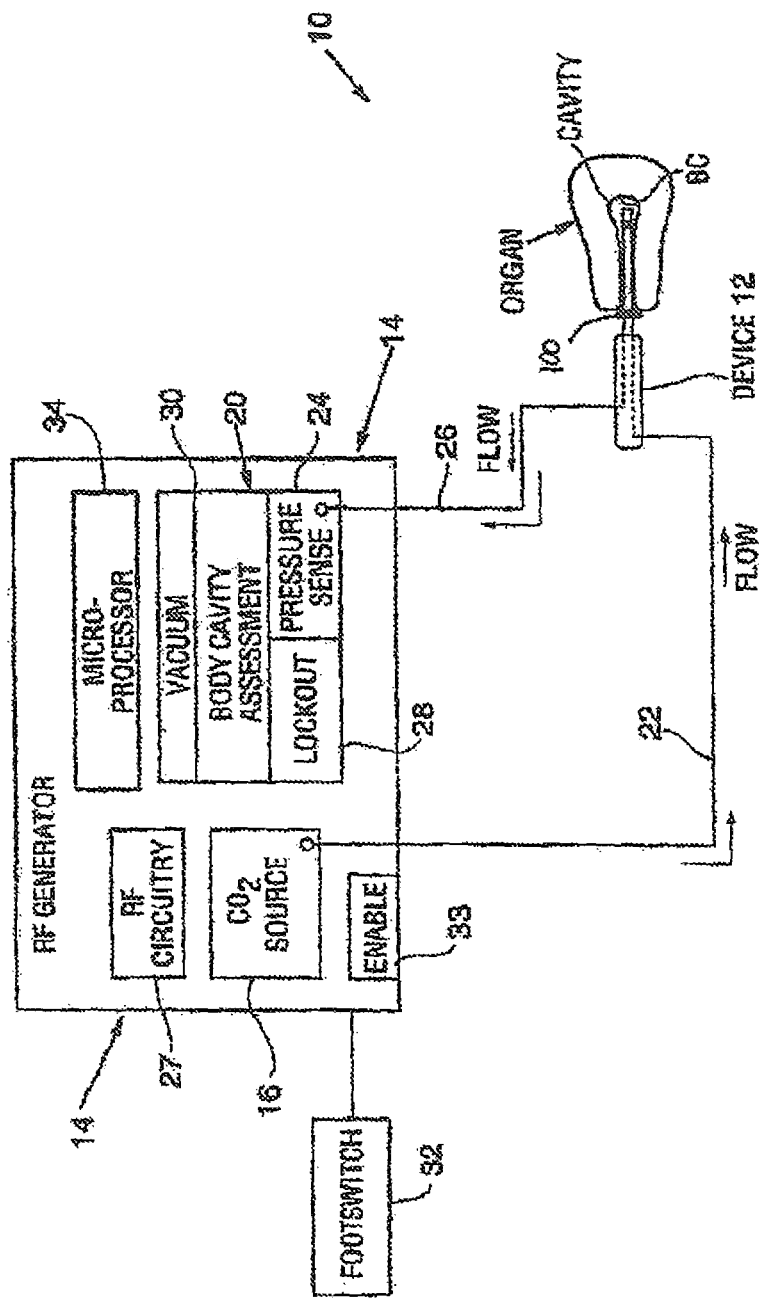
FIG. 1 is a schematic representation of a perforation detection system having a sealing device in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a perforation detection system 10 (also referred to as a "body cavity assessment system") that includes a sealing device 100 in accordance with embodiments described herein. In the illustrated embodiments, the system 10 forms part of an RF ablation system for ablating tissue within a body cavity such as a uterus. However, it should be appreciated that the perforation detection system 10 may be provided with another type of system used for treatment or diagnostic purpose, or it may be provided independently of a larger treatment or diagnostic system.

The perforation detection system 10 includes a medical ablation device 12 of a type used for tissue ablation, and a RF generator system 14 of the type used to deliver RF ablation energy to an electrode array on ablation device 12. The RF generator unit is provided with additional components that are used for assessing a condition of the body cavity. In particular, the RF generator unit is provided with a fluid/gas source 16 and a body cavity assessment system 20. Fluid/gas source 16 is fluidly coupled to ablation device 12 via a source line 22. The ablation device is positionable within a body cavity BC so as to deliver fluid/gas from source 16 through the source line 22 and the ablation device and into the body cavity.

Body cavity assessment system 20 includes a pressure sensing system 24 fluidly coupled to the medical device via pressure detection/signal line 26. Pressure sensing system 24 monitors the pressure within the body cavity BC while fluid/gas is being (or after it has been) delivered to the body cavity, and detects whether elevated pressure can be maintained above a predetermined threshold level over a predetermined period of time. If it cannot, the user is alerted that there may be a perforation in the organ. The sealing device 100 is for sealing the cervical opening while the pressure sensing system 24 is being operated.

Body cavity assessment system 20 further includes a lockout system 28 that prevents treatment with the ablation device 12 unless body cavity assessment has been performed (pre-test lockout) and that prevents treatment if the body cavity assessment indicates a possible perforation (post-test lockout). The RF generator system 14 is additionally provided with a vacuum system 30 coupled to pressure detection/signal line 26, RF circuitry 27, and other components needed to perform the ablation function. A footswitch 32 or other input device controls operation of the RF generator system 14. A microprocessor or programmable logic device 34 within the RF generator system 14 governs various functions, including the body cavity assessment, lockout, and RF ablation procedures.

Ablation Device

Figure 2A:
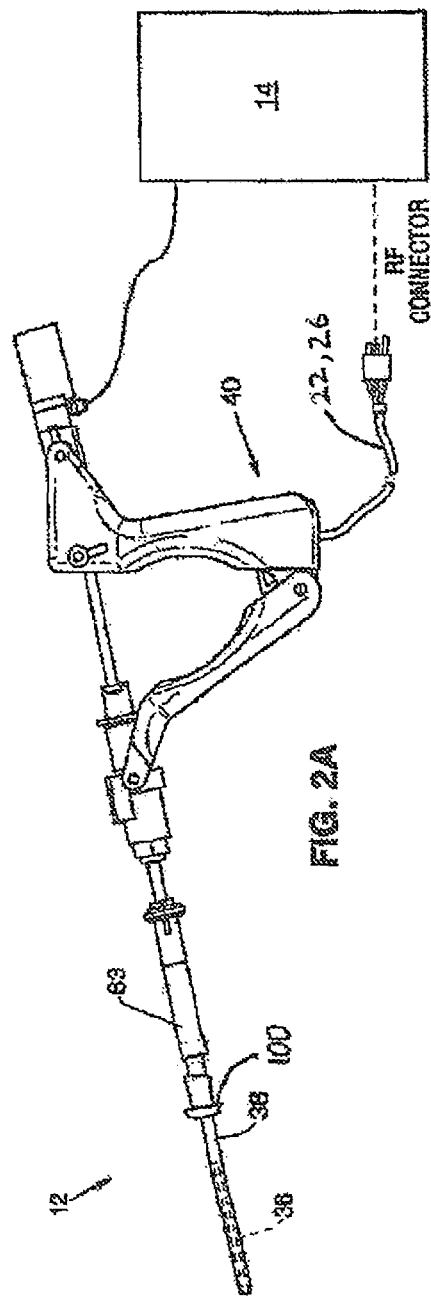
FIG. 2A is a side elevation view of an ablation device having a sealing device in accordance with some embodiments.
Figure 2B:
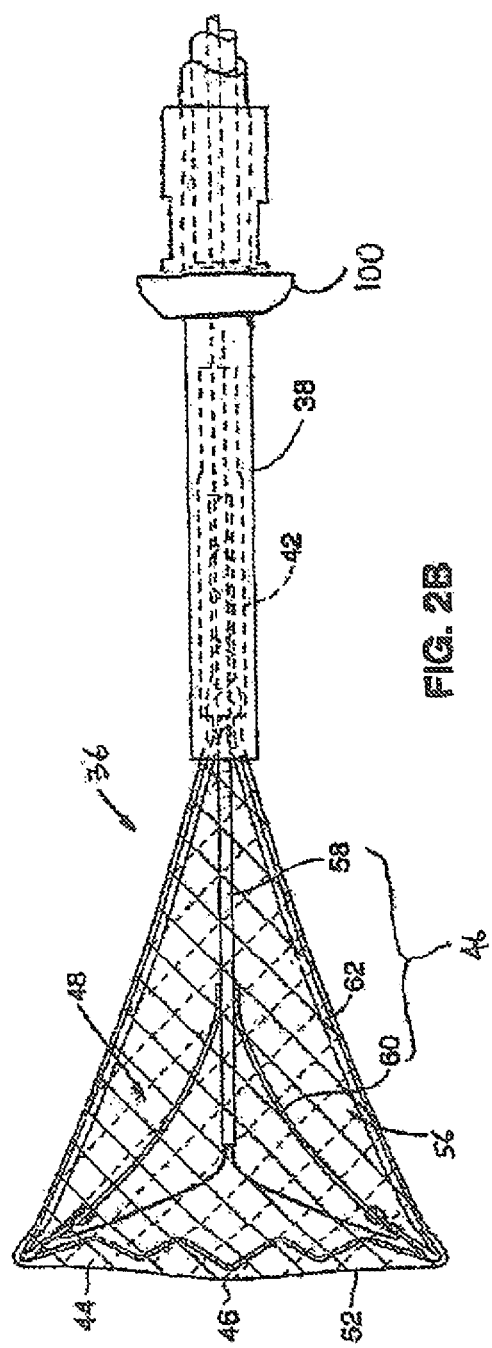
FIG. 2B is a plan view of the ablation device of FIG. 2A.

One example of an RF ablation device 12 that may be used with the system 10 is shown in FIGS. 2A and 2B. Ablation devices of this type are shown and described in U.S. Pat. Nos. 5,769,880 and 6,813,520, both of which are expressly incorporated herein by reference. A similar device is the NovaSure® ablation device available from Hologic, Inc. (www.hologic.com), Bedford Mass. The perforation detection system 10 may be provided in combination with other medical devices as well. Such alternative devices include thermal ablation devices in which heated liquid is circulated through a balloon positioned within the body cavity of interest, or other device used for procedures besides ablation. Alternatively, the perforation detection system 10 may be provided with two medical devices, one for use in delivering inflation medium and another for use in treating body tissue. As a further alternative, a treatment device may be provided independent of the system 10.

Ablation device 12 is configured to deliver RF ablation energy to the interior surface of a body cavity, while causing moisture (e.g., steam) generated during ablation to be withdrawn away from the body tissue—preferably using suction. This moisture transport feature of the device 12 is advantageous in that removing steam from the ablation site minimizes the amount of thermal ablation that would otherwise be caused by the steam. Greater control over ablation depth is thus achieved by allowing ablation to occur only (or primarily) by RF energy rather than by thermal conduction.

The device 12 includes an RF applicator head 36, a sheath 38, and a handle 40. The applicator head 36 is slidably disposed within the sheath 38 to give the applicator head 36 a streamlined profile (FIG. 2A) to facilitate insertion of the device into a body cavity (e.g., the uterine cavity). Once the applicator head 36 has been inserted into the body cavity, handle 40 is manipulated to cause the applicator head 36 to extend from the distal end of the sheath 38 and to expand into the position shown in FIG. 2B as to make contact with body tissue.

Referring to FIG. 2B, applicator head 36 extends from the distal end of sheath 38. Applicator head 36 includes an external electrode array 44 and an internal deflecting mechanism 46 used to expand and tension the array for positioning into contact with the tissue.

The array 44 is preferably formed of a stretchable metallized fabric mesh which is preferably knitted from a nylon and spandex knit plated with gold or other conductive material. In one array design, the knit is formed of three monofilaments of nylon knitted together with single yarns of spandex. Each yarn of spandex has a double helix of five nylon monofilaments coiled around it.

When in its expanded state, the array 44 includes a pair of broad faces 48 (one of which is shown in FIG. 2B) spaced apart from one another, and narrower side faces (not shown)

extending between the broad faces 48 along the sides and distal end of the applicator head 36, and a distal face 52 extends between the broad faces 48 at the distal end of the applicator head 36. Insulating regions (not shown) formed by etching or other techniques on the applicator head divide the mesh into electrode regions.

The array may be divided by the insulated regions into a variety of electrode configurations. In a preferred configuration, the insulating regions divide the applicator head into four electrodes by creating two electrodes on each of the broad faces.

Deflecting mechanism 46 and its deployment structure is enclosed within electrode array 44. Internal hypotube 58 is slidably and co-axially disposed within external hypotube 42 and internal flexures 60 are attached to internal hypotube 58. Flexures 62 extend from the external hypotube 42 on opposite sides of internal hypotube 58. Internal flexures 60 are attached to internal hypotube 58.

In the illustrated embodiment, the electrode array 44 is a knitted assembly. During use, moisture may pass through the spaces between the yarn of the knitted assembly and to be drawn into the exposed distal end of hypotube 58 using a vacuum source located in the RF generator system 14 and fluidly coupled to hypotube 58.

Each flexure 62 preferably includes conductive regions that are electrically coupled to the array 44 for delivery of RF energy to the body tissue. For example, strips of copper tape (not shown) or other conductive material may extend along opposite surfaces of each flexure. Conductor leads (not shown) are electrically coupled to the strips and extend through sheath 38 to an electrical cable which is attachable to the RF generator.

During use of the ablation device 12, the applicator head 36 is inserted into the uterus with the sheath 38 covering the array 44 to compress the applicator head 36 into a streamlined condition. Once the applicator head is within the uterus, the handle is used to withdraw the sheath and to open the array into its deployed position. Vacuum source 30 (FIG. 1) is activated, causing application of suction to hypotube 58. Suction helps to draw uterine tissue into contact with the array 44.

Ablation power is supplied to the electrode array 44 by the RF generator system 14. The tissue is heated as the RF energy passes from electrodes 56 to the tissue, causing moisture to be released from the tissue. The vacuum source helps to draw moisture from the uterine cavity into the hypotube 58. Moisture withdrawal is facilitated by the spaces in the knit array 44, by preventing moisture from being trapped between the array and the walls of the uterus.

During the operation of the ablation device 12, the sealing device 100 may help prevent fluid from leaking out of the uterus. In some cases, the sealing device 100 may also assist the vacuum source 30 in creating suction within the uterus during use.

Sealing Device

The sealing device 100 is configured (e.g., sized, shaped, and/or built) for sealing the cervical opening during an operation of the perforation detection system 10, such that the perforation detection system 10 can accurately detect the pressure within the uterus cavity. The sealing device 100 may have different configurations in different embodiments.

Figure 3A:
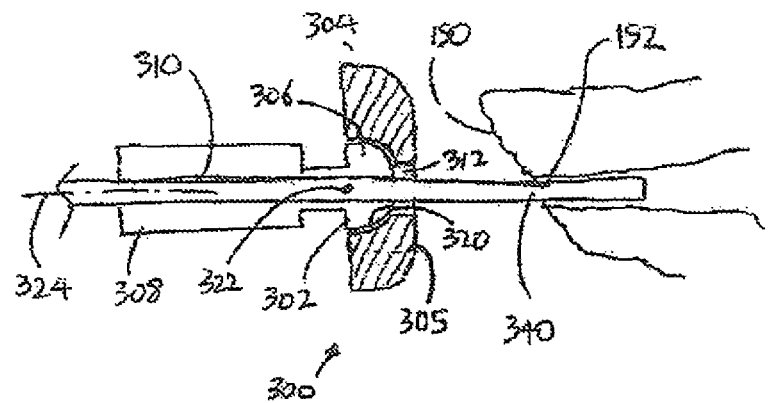
FIG. 3A illustrates a device for sealing a cervical opening in accordance with some embodiments.

FIG. 3 illustrates a sealing device 300 (an example of the sealing device 100) in accordance with some embodiments. The sealing device 300 may be considered a part of the perforation detection system 10, a part of the ablation device 12, or a device that is separate from the perforation detection system 10 and the ablation device 12. The device 300 includes a support structure 302, and a seal 304 coupled to the support structure 302. The seal 304 has a surface 305 for abutting against tissue 150 next to the cervical opening 152 during use. As used in this specification, the term "support structure" may refer to any device or component to which one or more components may be directly or indirectly coupled, and may or may not provide any support function (e.g., it may or may not provide any specific structural and/or functional support for other component(s)). The support structure 302 has a first end 306, a second end 308, and a lumen 310 extending between and through the ends 306, 308. The seal 304 includes an opening 312, which aligns with the lumen 310 of the support structure 302 such that a device 340 (e.g., a component of the perforation detection system 10 and/or a component of the ablation device 12, such as the sheath 38) may be extended therethrough. In some cases, the support structure 302 is detachably coupled to the device 340, which allows the support structure 302 to be used with another device that is different from the device 340. In some embodiments, the support structure 302 may be a part of the device 340.

Figure 3B:
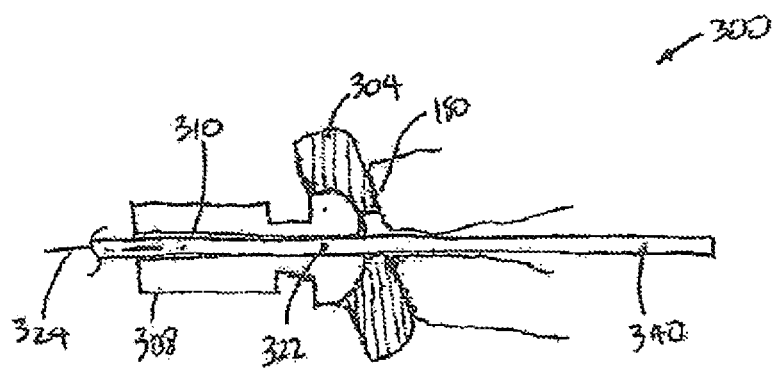
FIG. 3B illustrates the device of FIG. 3A abutting against tissue next to a cervical opening.

The first end 306 of the support structure 302 has a rounded configuration, which is configured (e.g., sized and shaped) to mate with a socket 320 of the seal 304, thereby allowing the seal 304 to be tiltable relative to the support structure 302. For example, the seal 304 may be tilted about an axis 322 that forms an angle with the longitudinal axis 324 of the support structure 302. In the illustrated embodiments, the seal 304 is rotatable relative to the support structure 302 in a plurality of directions. Such configuration is advantageous because it allows the seal 304 to automatically adjust to the angle of the external cervical opening 152, thereby achieving a complete seal at the interface (FIG. 3B). In cases where the tissue 150 of the os lacks firmness, the conforming seal 304 will also automatically align itself to the external os surface to whatever angle encountered at the external os. In some embodiments, the seal 304 is also effective for providing a seal for external cervical os that is patulous or uneven.

In other embodiments, instead of using the rounded end 306 and the socket 320, the device 300 can include another type of coupling that allows the seal 304 to be rotatably coupled to the support structure 302. For example, in other embodiments, the device 300 can include one or more hinges for rotatably coupling the seal 304 to the support structure 302. Also, in other embodiments, the seal 304 may have other shapes, such as a concave shape, a convex shape, a combination thereof, or any other shaped surface that aids in making a good seal with the external os. Thus, the mechanics of the conforming seal 302 need not be restricted to the examples shown in the figures, and the conforming seal 304 may have other configurations as long as the seal 304 is capable of assuming any angle relative to the longitudinal axis of the device to match the angle encountered at the external os of the cervix. In further embodiments, petroleum jelly impregnated gauze, or other related materials and devices may be used in conjunction with the conforming seal 304 if they aid in the sealing process.

Figure 4:
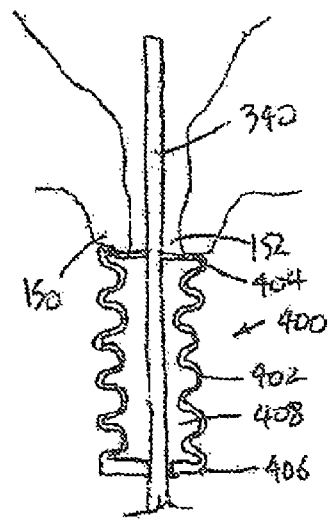
FIG. 4 illustrates another device for sealing a cervical opening in accordance with other embodiments.

FIG. 4 illustrates a sealing device 400 (another example of the sealing device 100) in accordance with some embodiments. The sealing device 400 may be considered a part of the perforation detection system 10, a part of the ablation device 12, or a device that is separate from the perforation detection system 10 and the ablation device 12. The device 400 includes a bellow 402 with a first end 404, a second end 406, and a lumen 408 extending between the ends 404, 406. The first end 404 of the bellow 402 is configured (e.g., sized and/or shaped) for abutting against tissue next to a cervical opening, thereby sealing the cervical opening. The lumen 408 allows a device 340 (e.g., a component of the perforation detection system 10 and/or a component of the ablation device 12, such as the sheath 38) to extend therethrough. As shown in the figure, the device 340 is an elongated member, such as a tube (e.g., for delivering object(s), device(s), and/or fluid), or a rod. In other embodiments, the device 340 may have other configurations. In some embodiments, the device 340, which may be a part of a medical device, functions as a support structure for providing support (e.g., carrying the bellow 402, or allowing the bellow 402 to be coupled thereto) for the bellow 402. Also, in some embodiments, the device 340 may be a part of the sealing device 400. For example, in some embodiments, the device 340 includes a central opening for receiving different medical devices, which allows the sealing device 400 to be used with different medical devices. The second end 406 of the bellow 402 is attached to the device 340, and the first end 404 is not, which allows the first end 404 to move relative to the second end 406.

During use, the device 340 is inserted through the vaginal opening and into the cervical opening. The device 340 is advanced distally until the first end 404 of the bellow 402 abuts against tissue 150 next to the cervical opening 152. The device 340 may then be further advanced distally so that the bellow 402 is compressed by pushing the first end 404 towards the second end 406. In the illustrated embodiments, the bellow 402 is made from a flexible material, which allows the bellow 402 to flex during use. In some cases, when the first sealing end 404 of the bellow 402 abuts against a cervical opening that is angled, the flexibility of the bellow 402 allows the first end 404 to conform with the angled cervical opening 152, thereby achieving a hermetic seal. For example, a first portion of the bellow 402 on one side of the bellow 402 may undergo more compression than a second portion of the bellow on another side of the bellow 402, thereby conforming to the angle of the cervical opening 152. Also, in some cases, the bellow 402 is effective for providing a seal for any cervical openings, including non-rounded cervical opening, or external cervical os that is patulous or uneven.

Figure 5A:
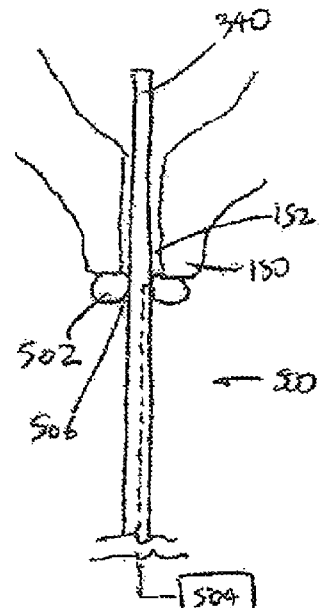
FIGS. 5A-5C illustrate another device for sealing a cervical opening in accordance with other embodiments.
Figure 5B:
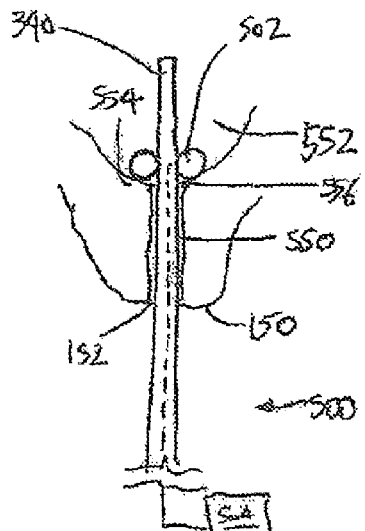
Figure 5C:
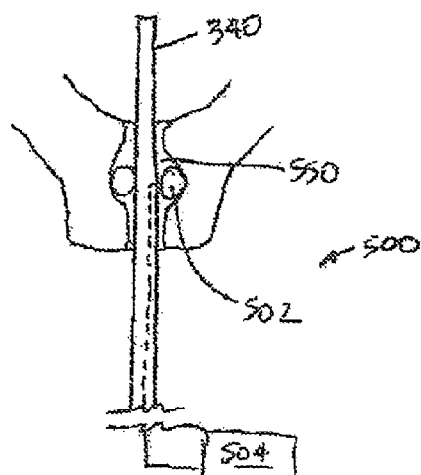

FIGS. 5A-5C illustrate a sealing device 500 (another example of the sealing device 100) in accordance with some embodiments. The sealing device 500 may be considered a part of the perforation detection system 10, a part of the ablation device 12, or a device that is separate from the perforation detection system 10 and the ablation device 12. The device 500 includes an inflatable member 502 that may be inflated during use to provide a sealing mechanism. The device 500 also includes a source 504 of inflation fluid (liquid, e.g., water, or gas, e.g., air) that is in fluid communication with a cavity of the inflatable member 502. The inflatable member 502 has a donut configuration with an opening 506, which allows a device 340 (e.g., a component of the perforation detection system 10 and/or a component of the ablation device 12, such as the sheath 38) to be extended therethrough. As shown in the figure, the device 340 is an elongated member, such as a tube (e.g., for delivering object(s), device(s), and/or fluid), or a rod. In other embodiments, the device 340 may have other configurations. In some embodiments, the device 340, which may be a part of a medical device, functions as a support structure for providing support (e.g., carrying the inflatable member 502, or allowing the inflatable member 502 to be coupled thereto) for the inflatable member 502. Also, in some embodiments, the device 340 may be a part of the sealing device 500. For example, in some embodiments, the device 340 includes a central opening for receiving different medical devices, which allows the sealing device 500 to be used with different medical devices.

It should be noted that the inflatable member 502 should not be limited to the donut configuration described previously, and that the inflatable member 502 may have other configurations in other embodiments, as long as the inflatable member 502, when inflated, can provide a seal for the cervical opening 152.

During use, the device 340 is inserted through the vaginal opening and into the cervical opening 152. The device 340 is advanced distally until the inflatable member 502 is adjacent the cervical opening 152. The inflatable member 502 is then inflated using the source 504 of the inflation fluid. The device 340 may then be further advanced until the inflated member 502 abuts against tissue 150 next to the cervical opening 152, thereby creating a seal at the cervical opening 152 (FIG. 5A). In some cases, the device 340 may be pushed distally further to press the inflated member 502 against the cervical tissue 150. Such technique allows the inflated member 502 to deform to conform with the tissue 150 next to the cervical opening 152. For example, pressing the inflated member 502 towards the tissue 150 may cause the inflated member 502 to deform to conform with an angled cervical opening 152, or with external cervical os that is patulous or uneven.

It should be noted that the inflatable member 502 may be positioned at other locations in other embodiments. For example, in other embodiments, the member 502, in its un-inflated configuration, may be inserted through the cervical canal 550. The member 502 is then inflated inside the uterus 552. The device 340 may then be pulled proximally until the inflated member 502 abuts against tissue 554 next to the internal cervical opening 556, thereby sealing the cervical opening 152/556 from inside the uterus 552 (FIG. 5B). In further embodiments, the member 502, in its un-inflated configuration, may be inserted into the cervical canal 550. The member 502 is then inflated at the cervical canal 550, thereby sealing the cervical opening from within the cervical canal 550 (FIG. 5C). In any of the embodiments described herein, the inflatable member 502 may be positionable, e.g., slidable, relative to the device 340, thereby allowing the position of the inflatable member 502 to be adjusted.

Figure 6A:
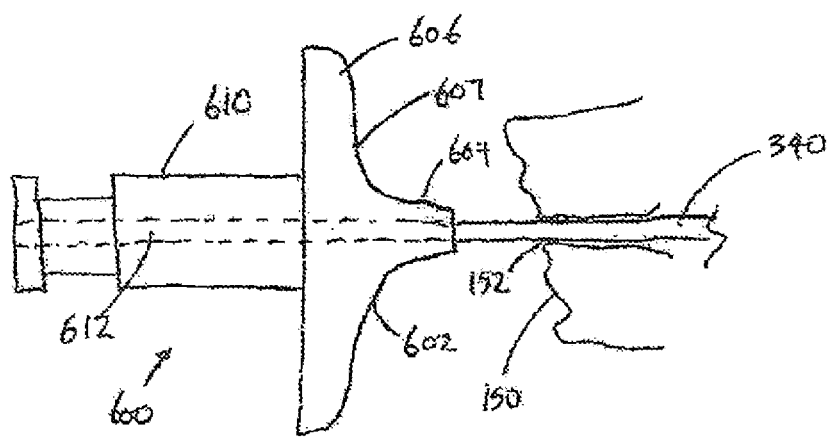
FIG. 6A illustrates another device for sealing a cervical opening in accordance with other embodiments.

FIG. 6 illustrates a sealing device 600 (another example of the sealing device 100) in accordance with some embodiments. The sealing device 600 may be considered a part of the perforation detection system 10, a part of the ablation device 12, or a device that is separate from the perforation detection system 10 and the ablation device 12. The device 600 includes a seal 602 having a tapered portion 604 for insertion at least partially into a cervical opening, and a cover portion 606 having a surface for abutting against tissue next to a cervical opening. As shown in the figure, the cover portion 606 extends radially away from the tapered portion 604, and has a cross sectional dimension that is at least 1.0 inch, and more preferably, at least 1.25 inches. Also as shown in the figure, the configuration of the seal 602 is such that the tapered portion 604 and the cover portion 606 form an inflection point 607.

The sealing device 600 also includes a support structure 610 to which the seal 602 is coupled. In some embodiments, the seal 602 is fixedly secured to the support structure 610. In other embodiments, the seal 602 may be moveably coupled to the support structure 610 such that the seal 602 may be positionable relative to the support structure 610. For example, the seal 602 may be rotatably coupled to the support structure 610, such as that described with reference to FIG. 3A. In the illustrated embodiments, the support structure 610 and the seal 602 have an opening 612 extending therethrough. The opening 612 allows a device 340 (e.g., a component of the perforation detection system 10, a component of the ablation device 12, such as the sheath 38, or a component of any other medical device) to be placed therethrough. In other embodiments, the support structure 610 itself may be a component of the perforation detection system 10, a component of the ablation device 12, or a component of any other medical device.

Figure 6B:
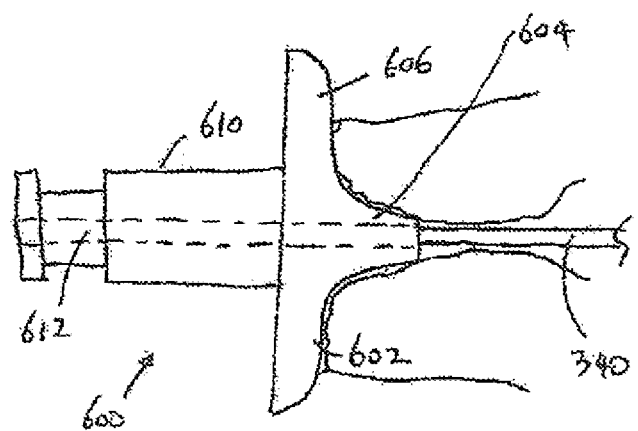
FIG. 6B illustrates the device of FIG. 6A abutting against tissue next to a cervical opening.

During use, the tapered portion 604 of the seal 602 is inserted into the cervical opening 152, and the cover portion 606 of the seal 602 is pressed against tissue 150 next to the cervical opening 152 to seal the cervical opening 152. The profile of the seal's 602 surface (with the inflection point 607) may resemble the profile of the tissue 150 next to the cervical opening 152, thereby increases the seal's 602 ability to form a complete seal. Also, because the additional sealing surface beyond the inflection point of the profile is almost perpendicular to the cervical opening 152, the cover portion 606 may be pushed against a patulous or uneven cervix, and may deform any malleable or soft tissue into a configuration that allows a seal to be formed (FIG. 6B). In some embodiments, the sealing device 600 is also effective for sealing any cervical openings, including non-rounded cervical openings.

As illustrated in the above embodiments, the sealing device 600 is advantageous because it obviates the need for a surgeon to create a seal by the use of tenaculum(s) or purse stitching the cervix to constrict tissue around a cervical collar, which are both traumatic processes. The sealing device 600 allows cervical seals that previously could not be created at all, or would require extensive troubleshooting, to be achieved easily.

Figure 7:
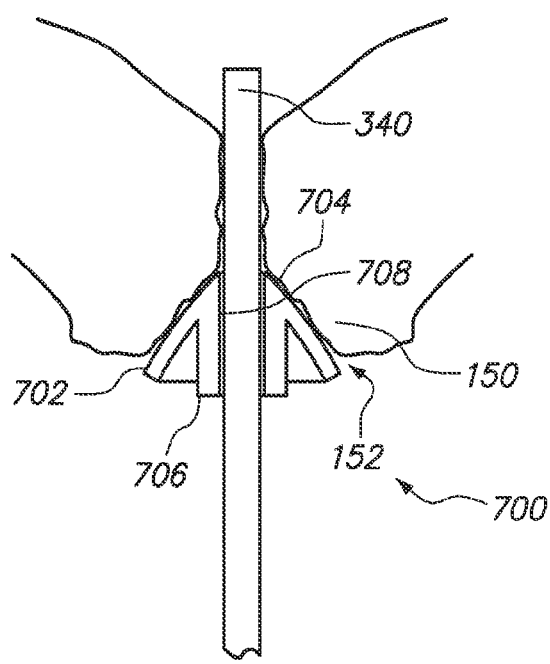
FIG. 7 illustrates another device for sealing a cervical opening in accordance with other embodiments.

FIG. 7 illustrates a sealing device 700 (another example of the sealing device 100) in accordance with some embodiments. The sealing device 700 may be considered a part of the perforation detection system 10, a part of the ablation device 12, or a device that is separate from the perforation detection system 10 and the ablation device 12. The device 700 includes a seal 702 with a first end 704, a second end 706, and a lumen 708 extending between the ends 704, 706. The first end 704 of the seal 702 for abutting against tissue 150 next to a cervical opening 152, thereby sealing the cervical opening 152. The lumen 708 allows a device 340 (e.g., a component of the perforation detection system 10 and/or a component of the ablation device 12, such as the sheath 38) to extend therethrough. As shown in the figure, the device 340 is an elongated member, such as a tube (e.g., for delivering object(s), device(s), and/or fluid), or a rod. In other embodiments, the device 340 may have other configurations. In some embodiments, the device 340, which may be a part of a medical device, functions as a support structure for providing support (e.g., carrying the seal 702, or allowing the seal 702 to be coupled thereto) for the seal 702. Also, in some embodiments, the device 340 may be a part of the sealing device 700. For example, in some embodiments, the device 340 includes a central opening for receiving different medical devices, which allows the sealing device 700 to be used with different medical devices.

In the illustrated embodiments, the seal 702 is made from a soft material. The soft material provides a flexible characteristic for the seal 702, such that when the seal 702 is inserted into the cervical opening 152, the seal 702 will conform to the shape of the cervical opening 152. Such configuration is especially effective for sealing any cervical openings, including non-rounded cervical openings.

Figure 8A:
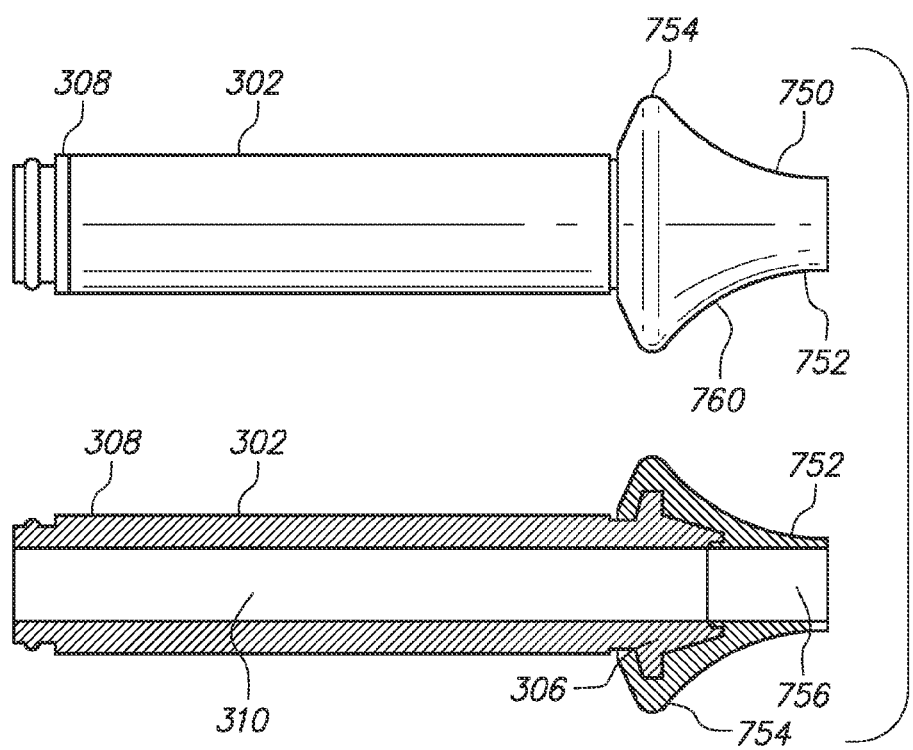
FIG. 8A illustrates another device for sealing a cervical opening in accordance with other embodiments.

FIG. 8A illustrates another embodiment of a seal 750 that includes a distal end 752, a proximal end 754, and a lumen 756 extending between the ends 752, 754. The proximal end 754 of the seal 750 has an enlarged configuration compared that to the distal end 752. As shown in the figure, the proximal end 754 of the seal 750 has a cavity for mating with a protrusion at the distal end 306 of the support structure 302. The seal 750 has a curvilinear surface 760 for abutting tissue at or near the cervical opening. In the illustrated embodiment, the seal 750 is made from an elastic material that allows the seal 750 to deform when pressed against the tissue at or near the cervical opening. In some cases, the material may be a soft material (e.g., a compliant material) such that the seal 750 will easily conform to the cervical tissue when the seal 750 is pressed against the tissue at or near the cervical opening. As shown in the figure, the seal 750 has a smooth transition from the distal end 752 to the proximal end 754. Such configuration allows the seal 750 to better conform to the profile of the tissue at or near the cervical opening, and to better provide a sealing at the cervical opening.

Figure 8C:
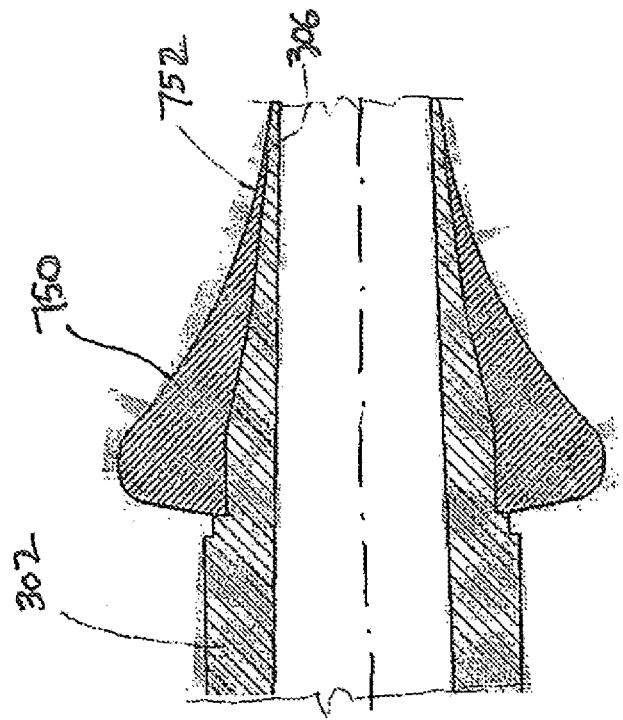
FIG. 8C illustrates a variation of the distal end of the device of FIG. 8A in accordance with other embodiments.
Figure 8B:
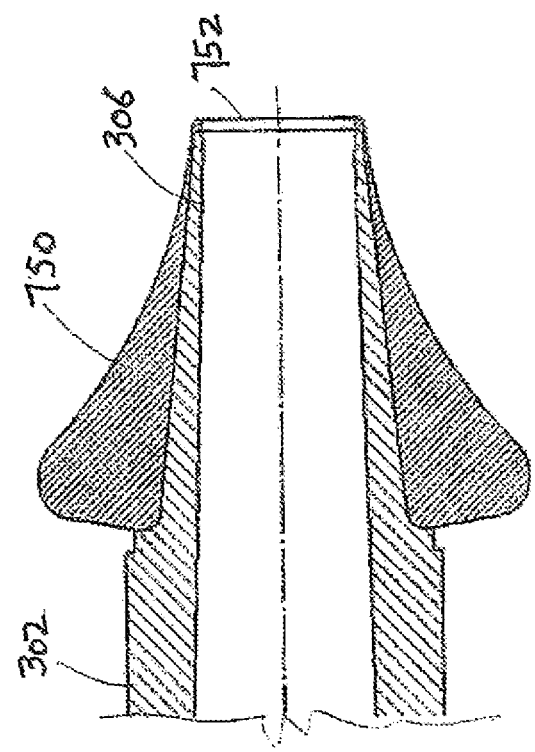
FIG. 8B illustrates a variation of the distal end of the device of FIG. 8A in accordance with other embodiments.

As shown in FIG. 8A, the distal portion of the seal 750 extends beyond the distal end 306 of the support structure 302. This offers the advantage of a softer tip. In other embodiments, as shown in FIG. 8B, the distal end 752 of the seal 750 may extend beyond and at least partially overlaps the distal end 306 of the support structure 302. This configuration also offers the advantage of a softer tip, while allowing a substantial portion of the seal 750 to be supported by the support structure 302. Alternatively, as shown in FIG. 8C, the distal end 752 of the seal 750 does not extend beyond the distal end 306 of the support structure 302. Instead, a portion of the support structure 302 extends beyond the distal end 752 of the seal 750, so that the seal 750 is fully seated on the support structure 302. This embodiment offers the advantage of enhanced rigidity at the tip, which prevents the seal 750 from invaginating and undesirably deforming during insertion and/or during storage (i.e. prior to use).

FIGS. 9A and 9B illustrate a sealing device 800 (another example of the sealing device 100) in accordance with some embodiments. The sealing device 800 may be considered a part of the perforation detection system 10, a part of the ablation device 12, or a device that is separate from the perforation detection system 10 and the ablation device 12. The device 800 includes a seal 802 having a distal portion 804 for insertion at least partially into a cervical opening. The distal portion 804 may have a tapered configuration as shown, or other configurations. The seal 802 also has a surface 806 for contacting tissue next to a cervical opening. As shown in the figure, the seal 802 also has an opening 808 formed on the surface 806, and a vacuum port 810. The opening 808 is in fluid communication with the vacuum port 810. In the illustrated embodiments, the opening 808 has a ring configuration, and is disposed circumferentially around a longitudinal axis 812 of the seal 802. In other embodiments, the opening 808 may have other configurations. For example, in other embodiments, the opening 808 may have a circular shape and is located on one side of the seal surface 806. In other embodiments, the seal surface 806 may have a plurality of openings 808 that are circumferentially disposed around the longitudinal axis 812 of the seal 802. In such cases, the openings 808 may be fluidly coupled to a common channel (not shown) formed inside the seal 802, and the channel is in fluid communication with the vacuum port 810.

The sealing device 800 also includes a support structure 820 to which the seal 802 is coupled. In some embodiments, the seal 802 is fixedly secured to the support structure 820. For example, the seal 802 and the support structure 820 may be formed together so that the sealing device 800 has a unity configuration. In some cases, the tubular structure may be considered to be a part of the seal 802. In other embodiments, the seal 802 may be moveably coupled to the support structure 820 such that the seal 802 may be positionable relative to the support structure 820. For example, the seal 802 may be rotatably coupled to the support structure 820, such as that described with reference to FIG. 3A. In such cases, the support structure 820 may be considered to be a part of the sealing device 800, or a part of the device 340. Also, in some cases, the device 340 may be considered a support structure. In the illustrated embodiments, the support structure 820 and the seal 802 have an opening 822 (shown in FIGS. 10 and 11) extending therethrough. The opening 822 allows the device 340 (e.g., a component of the perforation detection system 10, a component of the ablation device 12, such as the sheath 38, or a component of any other medical device) to be placed therethrough. In other embodiments, the support structure 820 itself may be a component of the perforation detection system 10, a component of the ablation device 12, or a component of any other medical device.

FIG. 10 illustrates the sealing device 800 being used to seal a cervical opening that has a normal configuration. During use, the distal portion 804 of the seal 802 is inserted into the cervical opening 152, such that the surface 806 of the seal 802 contacts against tissue 150 next to the cervical opening 152 to seal the cervical opening 152. The tapered configuration of the seal 802 allows the seal 802 to be used with cervical opening 152 of any size. In some cases, to assist forming a seal against the cervical tissue, the vacuum port 810 may be coupled to a vacuum source 880, which provides a suction force to pull tissue towards the opening 808 of the seal 802. Because the opening 808 is disposed circumferentially around the longitudinal axis of the seal 802, the cervical tissue around the os is circumferentially pulled towards the seal 802, thereby creating a seal around the os.

FIG. 11 illustrates the sealing device 800 being used to seal a cervical opening that has an angled configuration. During use, the distal portion 804 of the seal 802 is inserted into the cervical opening 152, such that the surface 806 of the seal 802 contacts against tissue 150 next to the cervical opening 152 to seal the cervical opening 152. In some cases, to assist forming a seal against the cervical tissue, the vacuum port 810 may be coupled to the vacuum source 880, which provides a suction force to pull tissue towards the opening 808 of the seal 802. Because the opening 808 is disposed circumferentially around the longitudinal axis 812 of the seal 802, the cervical tissue around the os is circumferentially pulled towards the seal 802, thereby creating a seal around the os. Also as shown in the illustrated embodiments, because the opening 808 is located sufficiently distal at the seal 802 such that the opening 808 is still next to the cervical tissue at the angled portion 884 (i.e., the portion 884 that is further away from the seal 802 axially), the opening 808 can still be used to create a suction force to pull the cervical tissue towards the seal 802.

As illustrated in the above embodiments, the sealing device 800 is advantageous because it obviates the need for a surgeon to create a seal by the use of tenaculum(s) or purse stitching the cervix to constrict tissue around a cervical collar, which are both traumatic processes. The sealing device 800 allows cervical seals that previously could not be created at all, or would require extensive troubleshooting, to be achieved easily. In some embodiments, the sealing device 800 is also effective for sealing any cervical openings, including non-rounded cervical openings, and/or openings with an angled configuration.

Pneumatic Subsystem

As discussed, the sealing device 100 (such as any of sealing devices 300-700) is configured for sealing the cervical opening during an operation of the perforation detection system 10, such that the perforation detection system 10 can accurately detect the pressure within the uterus cavity. Components and features of the perforation detection system 10 that operate in conjunction with the sealing device 100 will now be described.

Figure 12:
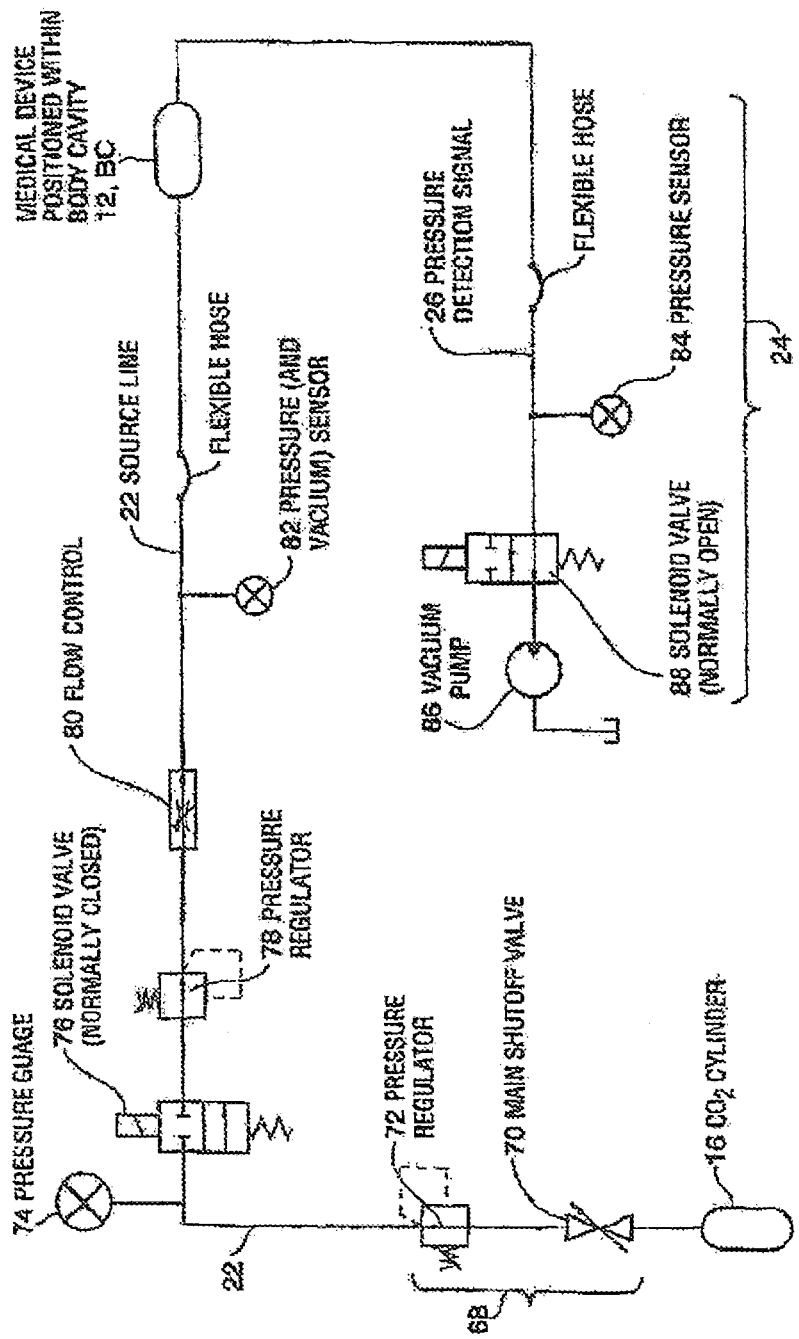
FIG. 12 is a schematic representation of the pneumatic subsystem of the system of FIG. 1.

The fluid/gas source 16, pressure sensing system 24 and associated components are shown in FIG. 12. Each of the components of the pressure sensing system 24 is preferably coupled to microprocessor 34 of the RF generator system 14 although for clarity the microprocessor is not shown in FIG. 12. All pressure transducers, solenoid valves, and the vacuum pump are controlled by the microprocessor. As discussed, a programmable logic device may be used in place of the microprocessor, although the term "microprocessor" will be used here for simplicity.

It is also important to note that in the embodiment described below the two lines (source line 22 and pressure detection/signal line 26) play different roles during RF ablation than for perforation detection. Specifically, the signal line 26 for perforation detection serves as a suction line for ablation. The source line 22 for perforation serves as a vacuum signal line for ablation.

Components along the source line 22 will first be described. Fluid/gas source 16 is preferably a disposable $CO_2$ cylinder, and may be a 16 gm cylinder providing approximately 850 psi at 25 C. One such example is the Linde medical grade 16 gm cylinder. The cylinder is removably attached to a pressure regulator 68 such as the Leland Model 50033 or equivalent. Regulator 68 includes a main shutoff valve 70 and pressure regulation component 72 which has a control pressure of approximately 60 psi. A pressure gauge 74 such as SenSym model ASCX100DN or equivalent is fluidly coupled to source line 22. Pressure gauge 74 monitors the pressure remaining in the fluid/gas source 16 so as to detect when a low volume of fluid/gas remains, or when the user has failed to open the valve 70.

A solenoid valve 76 is positioned along the source line 22, downstream of the pressure regulator 68. Valve 76 remains in a closed condition, preventing flow of gas through the line 22, except when a cavity assessment procedure is being carried out. A second pressure regulator 78, such as an Airtrol R-920 series regulator, is positioned downstream of the valve 76 so as to reduce pressure in line 22 down to approximately 90+/−10 mmHg during a cavity assessment procedure. A flow control orifice 80, positioned downstream of regulator 78, limits flow in line 14 to 100+/−10 scc/min (standard cc/min). A pressure sensor 82 downstream of orifice 80 monitors whether the pressure limit (of, for example, approximately 100 mm Hg) has been exceeded. If the limit has been exceeded, an output signal from this sensor causes an audible alarm to be triggered and the solenoid valve 76 is turned off. Downstream of orifice 80, source line 22 is coupled, using a flexible Tygon® tubing for example, to the introducer sheath 38 (FIG. 2B) of the ablation device 12. The introducer sheath is located at the internal surface of the body cavity BC (the internal os, for example, in the case of a uterine cavity) so as to deliver gas into the body cavity BC that is to be treated.

Turning to the components along the pressure detection line 26, the pressure signal line 26 is fluidly coupled, using a Tygon® tubing for example, to the lumen of hypotube 58. Downstream of the medical device 12 is a pressure sensor 84, such as the SenSym ACSX05DN. During a cavity assessment procedure, sensor 84 monitors pressure in the pressure signal line 26 and delivers the signal to microprocessor 34. Microprocessor 34 (or other electronic means such as the programmable logic device mentioned previously) then determines if pressure in the body cavity BC has failed to achieve a predetermined threshold (indicating a perforation in the body cavity) or if it has and maintained the threshold for a predetermined time period (indicating that the body cavity has no perforation). In this capacity, the microprocessor or (programmable logic device) serves as a feedback means that activates a notification signal to alert a user if the pressure monitored by the pressure sensor fails to rise and remain above a predetermined level during a predetermined amount of time. The microprocessor may initiate various forms of notification signals, such as visual or auditory signals.

Further downstream of the pressure sensor 84 is a vacuum pump 86. While not needed for perforation detection, vacuum pump 86 is used to carry out the moisture transport function of the medical device 12 described in the section entitled Ablation Device above.

A second solenoid valve 88 lies upstream of the vacuum pump 86. Valve 88 remains open at all times except during cavity assessment. Because the exhaust line of the vacuum pump may not be air-tight when it is not operating (including during the cavity assessment procedure) the valve 88 is provided to close the pressure signal line against leaks through the vacuum pump. During the cavity assessment procedure, the cavity is pressurized by opening 76 and closing 88, then after a certain pressurization period 76 is closed and structures 22-12-26 make a hermetically sealed system (assuming seal 100 works effectively). Any leakage out of the 22-12-26 system is then detected by sensor 84.

Figure 13:
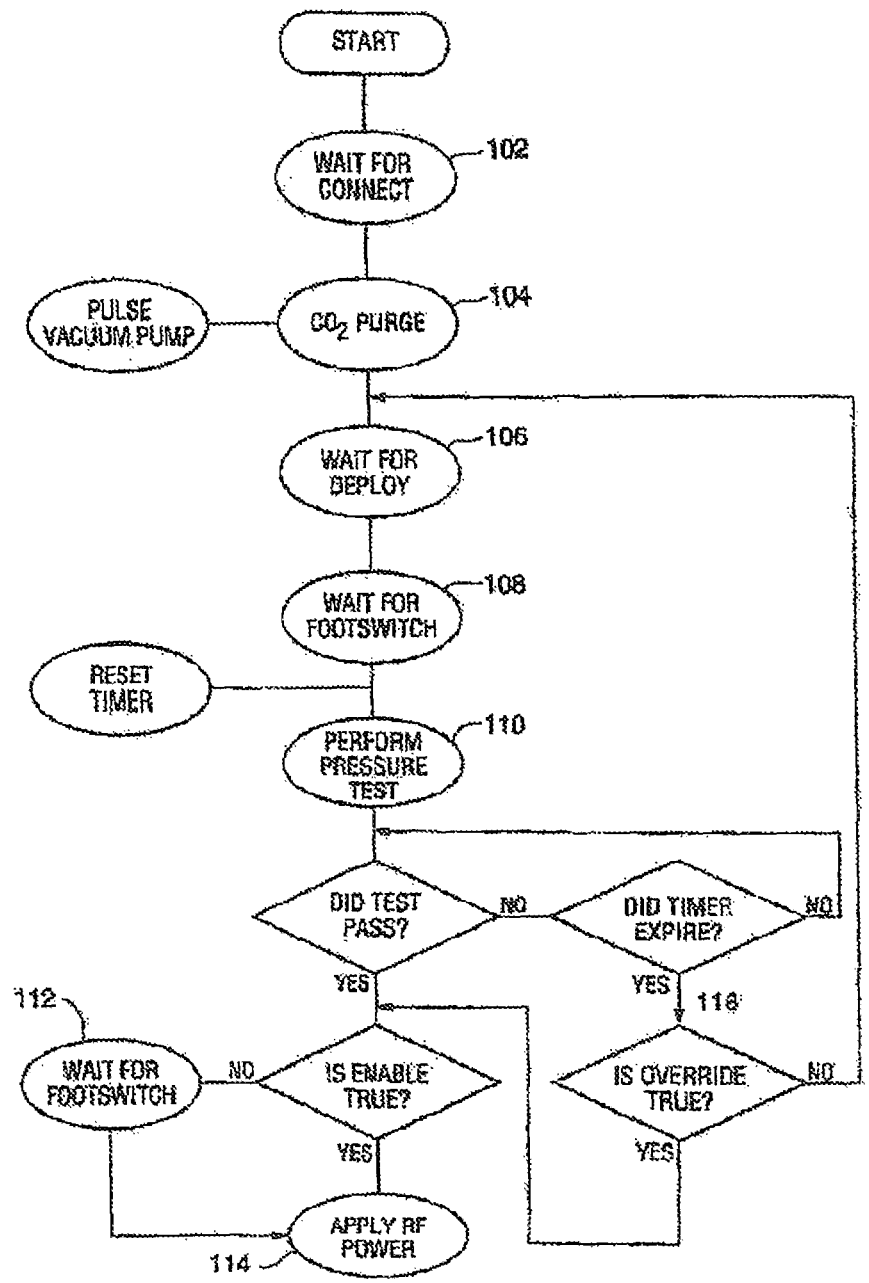
FIG. 13 is a simplified state diagram illustrating a mode of operation utilizing perforation detection and lockout features.

A simplified state diagram illustrating operation of the system is shown in FIG. 13. Operation begins with valve 76 in the closed condition, and with valve 88 in the opened condition. In preparation for use of the system, a $CO_2$ cylinder 16 is connected to the appropriate receiving device on the RF Generator's pneumatic subsystem (FIG. 13). The power to the generator is switched on. Pressure gauge 74 detects the pressure in the portion of pressure/monitoring line 22 extending between $CO_2$ cylinder 16 and valve 76. If the user has failed to open the main $CO_2$ shutoff valve 70, or if the pressure detected by gauge 74 is less than the specified pressure, an audible alert will sound, indicating a low-gas condition. Assuming no low-gas condition is detected, the user will connect the ablation device 12 to the RF generator system 14.

The system remains in a "WAIT FOR CONNECT" condition, step 102, until the user connects the ablation device 12 to the RF generator system. When the ablation device is plugged in, it actuates a microswitch or similar feature, which alerts the microprocessor that the ablation device has been connected. Connection of the device automatically starts the "CO2 PURGE" cycle, step 104. During the purge cycle, valve 76 is opened to permit the flow of $CO_2$ through the device to drive air from the device. The purge cycle lasts for a duration sufficient to purge the air from the system, approximately 10 seconds. During the purging cycle the user is alerted by audible and visual indicators not to insert the device into the body cavity in order to prevent air from being delivered into the body. As a safety precaution, the vacuum pump that is part of the RF Controller is pulsed every few seconds during purging. If the user has inserted the ablation device into a body cavity during purging, the vacuum pump will draw out air that is delivered to the body.

During the purge cycle and device insertion into the body cavity, the ablation device is closed, such that the poles of the electrode array are in contact with each other. A low voltage signal is applied to the ablation device which senses that the poles are in contact by detecting a DC short. After the completion of the purging cycle the system waits for the device to be deployed within the patient, step 106, by monitoring for the end of the DC short condition. Once the user inserts the device into the uterine cavity and opens the array, the system detects that a DC short condition is no longer present. As a safety precaution, the perforation detection cycle cannot be initiated until the DC short condition is eliminated. In this way the last operation to be performed before the application of RF energy is the perforation detection cycle.

From the completion of the purge cycle to the initiation of the perforation detection test, a continuous, low level flow of CO2 is circulated through the ablation device to keep the source and pressure signal lines open and free from blockage.

Next, the system waits for the user to depress the footswitch 32, "WAIT FOR FOOTSWITCH", step 108. Once the footswitch has been depressed, a 30-second timer is initialized ("RESET TIMER") and the perforation detection test, ("PERFORM PRESSURE TEST") 110 begins. Valve 88 is energized to close off the vacuum pump 86 to avoid loss of pressure through it. If it was not already opened, valve 76 is opened, allowing $CO_2$ to flow into the body cavity via medical device 12. When the pressure at gauge 84 rises and remains above 50 mmHg for 4 seconds, the test has passed and the system moves to a "PASSTHROUGH" state. It should be noted that the system may alternatively pressurize the cavity, seal it off and terminate flow into the cavity, and then detect whether the monitored pressure falls below a predetermined level within a predetermined time period, indicating that a perforation may be present. As illustrated in FIG. 13, the "PASSTHROUGH" condition cannot be reached unless the body cavity assessment has been performed. In this capacity, the perforation detection system circuitry and logic components function as a pre-test lockout means.

In the "PASSTHROUGH" condition the $CO_2$ is turned off and the vacuum pump is re-enabled by re-opening valve 88. If the ENABLE button 33 has been pressed (automatic mode), RF power 114 ("APPLY RF POWER") will be delivered automatically to the array 44 once the cavity assessment cycle has been completed and passed. If the ENABLE button has not been depressed (semiautomatic mode), the system moves through the "PASSTHROUGH" state and waits for footswitch actuation 112 ("WAIT FOR FOOTSWITCH"). The user must press the button to enable the RF generator and then press the foot switch 32 (FIG. 1) to deliver RF power 114.

In the event the cavity assessment test is not passed after the 30 second timer has expired, an audible tone sounds and visual indicators flash. The system remains in a TEST FAIL state, step 116, and awaits further action by the user. If the user presses the foot switch, the system re-sets to the initial ready state, step 108, with the $CO_2$ flow off. The user may attempt the cavity assessment sequence as many times as desired. As FIG. 13 illustrates, the perforation detection system circuitry and logic components function as a post-test lockout means preventing delivery of RF power using the ablation device if the body cavity assessment is run but not passed.

Alternatively, after one or more cavity assessment procedures has been performed and failed, the user may choose to activate a form of override means to override the post-test lockout means and cause the system to deliver RF energy despite the cavity assessment test having been failed. To do so, the user will press and hold the ENABLE button 33 (FIG. 1) for six seconds. Note that the pressure check must be attempted at least one time before this feature is available. If the user overrides the cavity assessment, the system moves to the "PASSTHROUGH" state to wait for footswitch step 112. In other embodiments, the override feature is optional, and the system does not include the override feature.

If at any time during the above sequence, the user should close the ablation device, a DC short will be detected in the electrode array by the RF generator's DC short detection circuitry. Closing the device causes the state of the perforation test to change to fail, and the system resets to the "WAIT FOR DEPLOY" state, step 106. The system will then require that cavity assessment be performed again once the array is reopened. This assures that the last step performed before the application of RF energy is the perforation detection test: if the user, after having successfully completing the test, decides to close and remove the device for any reason, the perforation detection test must be performed again once the device is deployed in the body cavity. This requirement also prevents a user from abusing the system by running cavity assessment with the device outside the body, and then inserting the device, overriding the test, and ablating without having ever performed cavity assessment within the body cavity.

There are several features that improve the system's ease of use. Firstly, the physician can start or stop the perforation test at any time in the sequence. Secondly microprocessor 34 is capable of distinguishing the difference between a device that is closed versus a device that is undergoing slight motion in the body cavity, thus reducing the likelihood that a passed test condition will be overturned. Finally, the system includes a collar assembly 63 in FIG. 2A which is capable of sealing the entry into the body cavity BC if leaks are determined to exist, thus reducing the likelihood of a false test failure. The system also includes a seal (not shown) between elements 63 and 38 for preventing fluid (e.g., gas) from leaking out at the gap that is between the collar assembly 63 and the shaft.

In the above embodiments, the sealing devices 300, 400, 500, 600, 700 have been described with reference to sealing a cervical opening 152. However, in other embodiments, any of these sealing devices may be used to seal other bodily openings, such as the virginal opening, the anus opening, etc. Thus, any of the sealing devices 300-700 may have any size and/or shape that is suitable for a particular application. Also, in other embodiments, any of the sealing devices 300-700 may be a part of an ablation device that has a different configuration from that described with reference to FIG. 2. In further embodiments, instead of being a part of the perforation detection system 10 or a part of the ablation device 12, any of these sealing devices may be a part of other medical device, which may be a treatment device, a diagnostic device (e.g., an imaging device, a biopsy device, etc.), or a device with both treatment and diagnostic capabilities.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the scope of the present inventions as defined by the claims.

What is claimed:

1. A device for sealing a cervical opening of a uterus, comprising:
   an elongate support structure having a proximal end and a distal end, and defining an axial lumen therethrough in communication with an opening in the distal end;
   a sealing member, the sealing member having a distal surface configured for contacting tissue surrounding the cervical opening, and a proximal surface configured to receive the distal end of the elongate support structure, wherein the distal end of the elongate support structure is configured to seat within and thereby form a seal with the proximal surface of the sealing member, and wherein the sealing member may be tilted relative to the distal end of the support structure to maintain a seal when the elongate support structure is not orthogonal with the tissue surrounding the cervical opening, the sealing member having a central opening therein so that the axial lumen of the support structure is in communication with an interior region of the uterus via the open end of the elongate support structure when a seal is formed by the elongate support structure and sealing member; and
   an ablation device disposed within the axial lumen of the elongate support structure and the central opening of the sealing member, the ablation device comprising an expandable distal portion configured to expand when the distal portion of the ablation device is disposed within the uterus.

2. The device of claim 1, wherein the distal end of the elongate support structure has a rounded configuration, and wherein the sealing member is rotatably coupled to the distal end of the elongate support structure while a seal is formed by the elongate support structure and sealing member.

3. The device of claim 1, wherein the distal end of the elongate support structure comprises a convex surface, and the proximal surface of the sealing member comprises a concave surface.

4. The device of claim 1, further comprising a tubular member disposed within the axial lumen of the elongate support structure, the tubular member configured to allow passage of devices, agents or fluid into the uterus.

5. A device for sealing a cervical opening of a uterus, comprising:
   an elongate support structure having a proximal end and a distal end, and defining an axial lumen therethrough; and
   a tapered sealing member rotatably carried on the distal end of the support structure, the tapered sealing member comprising an outer surface and an inner surface, the inner surface defining a central axial lumen through which the elongate support structure extends, the outer surface configured for contacting tissue surrounding the cervical opening and comprising one or more openings therein, wherein each of the one or more openings is in fluid communication with a vacuum port, such that a vacuum source placed in fluid communication with the vacuum port would cause cervical wall tissue to be drawn against, and thereby form a seal with, the outer surface of the sealing member,
   wherein the elongate support structure may be rotated relative to the sealing member, while a seal is maintained between the outer surface of the sealing member and cervical wall tissue.

6. The device of claim 5, wherein the one or more openings comprise a plurality of openings distributed circumferentially about the outer surface of the sealing member.

7. The device of claim 5, wherein the one or more openings are in fluid communication with a common channel, and the common channel is in fluid communication with the vacuum port.

8. The device of claim 7, wherein the common channel comprises a ring configuration disposed within the sealing member.

9. The device of claim 5, further comprising a pressure sensing device coupled to the sealing member.

10. The device of claim 5, further comprising a tubular member disposed within the axial lumen of the elongate support structure, the tubular member configured to allow passage of devices, agents or fluid into an interior region of the uterus.

11. The device of claim 5, further comprising an ablation device disposed within the axial lumen of the elongate support structure, the ablation device comprising an expandable distal portion configured to expand when the distal portion of the ablation device is disposed within the uterus.

* * * * *